United States Patent [19]

Lacey et al.

[11] Patent Number: 5,749,360
[45] Date of Patent: May 12, 1998

[54] TRACHEOSTOMY MASK WITH TRACHEOSTOMY TUBE ALIGNMENT STABILIZER

[75] Inventors: William J. Lacey, Stuart, Fla.; John Elkins, St. James, N.Y.

[73] Assignee: Hospitak, Inc., Farmingdale, N.Y.

[21] Appl. No.: 794,606

[22] Filed: Feb. 3, 1997

[51] Int. Cl.⁶ .......................... A61M 16/00; A62B 9/06
[52] U.S. Cl. .................. 128/207.14; 128/207.17; 128/200.26
[58] Field of Search ............... 128/200.26, 207.14, 128/207.17, 207.29, 912, DIG. 26

[56] References Cited

U.S. PATENT DOCUMENTS

| 3,667,475 | 6/1972 | Venturelli et al. |
| 3,824,999 | 7/1974 | King |
| 4,274,406 | 6/1981 | Bartholomew |
| 5,022,394 | 6/1991 | Chmielinski |
| 5,027,811 | 7/1991 | Tuxill |
| 5,458,139 | 10/1995 | Pearl |
| 5,485,837 | 1/1996 | Solesbee et al. |

*Primary Examiner*—Kimberly L. Asher
*Attorney, Agent, or Firm*—Hoffmann & Baron, LLP

[57] ABSTRACT

A tracheostomy mask for delivering gaseous therapeutics to a patient fitted with an tracheostomy tube includes a mask body and an alignment stabilizer. The mask body has an opening to receive oxygen and humidification to be delivered to a patient. The alignment stabilizer is supported by the mask body and maintains alignment between the mask body and the tracheostomy tube inserted within the neck of a patient. By maintaining this alignment, the tracheostomy mask with alignment stabilizer insures reliable therapeutic delivery to the patient.

4 Claims, 4 Drawing Sheets

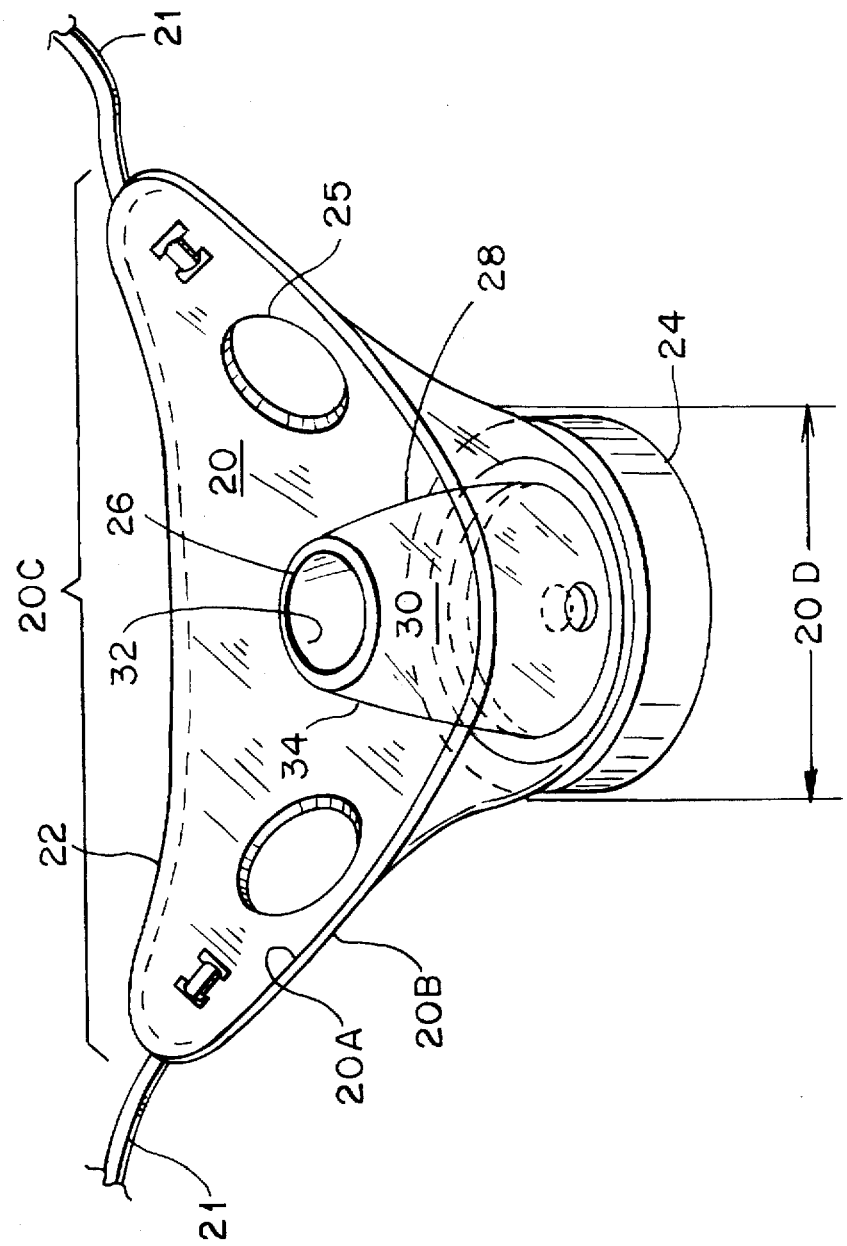

TRACHEOSTOMY MASK WITH TRACHEOSTOMY TUBE ALIGNMENT STABILIZER

BACKGROUND OF THE INVENTION

1. Field of the Invention

The present invention relates generally to apparatus in the field of respiratory therapy, and more particularly relates to a tracheostomy mask including a stabilizer for improved alignment with a tracheostomy tube.

2. Description of the Prior Art

Medical patients who suffer from an obstruction in the respiratory tract are often treated with surgery to create an opening in the neck through which the patient breaths. The result of the surgery is a stoma or breathing hole in which the patient is often intubated with a tracheostomy tube. As the mouth and nose are bypassed in this procedure, it is desirable to add supplemental humidification to the air which is being introduced through the tracheostomy tube. Also, such patients often require the infusion of a gaseous medicament, such as oxygen, which may also be supplied into the tracheostomy tube.

The gaseous medicament and humidification (therapeutics) are typically introduced through a mask which is coupled to a supply of therapeutics. Such a mask is described in U.S. Pat. No. 3,236,236 to Hudson. FIGS. 1A and 1B illustrate a mask formed substantially according to the Hudson patent in cooperation with a patient's neck. The Hudson mask includes a mask body 4 which is formed from flexible plastic in the shape of a concave shell. The mask body 4 has a forward portion and a rear portion. The rear portion of the mask body 4 is engaged about the neck of a patient by a thin elastic strap 6. The forward portion of the mask body 4 has an opening 12 to receive the required therapeutics. A supply tube 8 is affixed to the mask body 4. The supply tube 8 extends away from the patient and transports the therapeutics from the supply to the patient.

In order to function properly, the supply tube opening 12 must substantially align with a tracheostomy tube 1 inserted in the neck of the patient. However, the mask disclosed by Hudson does not contain any mechanism for providing the required alignment between the supply tube opening 12 and the tracheostomy tube 1. As a result, it is possible for a mask formed in accordance with the Hudson patent to shift around the patient's neck and disrupt the alignment between the supply tube opening 12 and tracheostomy tube 1.

An example of this misalignment is illustrated in FIG. 1B. The danger associated with this misalignment is that the medicament and humidity from the supply tube 8 may no longer be infused to the patient. The mask further includes holes 10 which are provided in the mask body 4 to prevent excess humidity expelled by the patient from collecting within the mask. As FIG. 1B illustrates, if a hole 10 aligns with the tracheostomy tube 1, the patient is likely to inhale ambient air from the outside environment rather than the therapeutics from the supply tube 8.

U.S. Pat. No. 5,485,837 to Solesbee discloses a trachea mask and neck strap combination which fixes the relative position of the tracheostomy tube and mask body. The mask body of the Solesbee patent is essentially that which is disclosed in Hudson. The Solesbee patent further includes a strap which is affixed to the tracheostomy tube and secured about the patient's neck. The mask body is affixed to the strap, and thereby to the tracheostomy tube, by "VELCRO" (™) hook and loop fasteners or similar fastening means. Because the mask is rigidly affixed to the tracheostomy tube by the strap, any force which is applied to the supply tube will be transferred to the mask and subsequently to the tracheostomy tube. This may result in discomfort and possible injury to the patient. As the supply tube extends from the mask, to equipment which is remote from the patient, this disadvantage is significant.

U.S. Pat. No. 5,027,811 to Tuxill discloses a trachea mask with a fluid collecting chamber. The trachea mask of the Tuxill patent has a forward mask body which is similar to that of Hudson. The Tuxill patent further includes a plenum which is sealed about the rear perimeter of the mask body, thereby forming a chamber with the mask body. The plenum includes an opening which fits over the tracheostomy tube and places the opening of the tracheostomy tube within the chamber. By forming a closed chamber, fluids expelled by the patient through the tracheostomy tube may be contained. This containment minimizes potential fluid contact with health care providers.

While fluid containment is an advantage for patients suspected or known to have communicable diseases, the plenum creates an interface with substantial surface area contacting the neck of the patient. In order to achieve the desired goal of fluid containment, the plenum must be fabricated from a material which is non-porous. The extended non-porous (non-breathable) interface prevents ventilation to the skin underneath the plenum. Because trachea masks are extended wear treatment devices, the non-breathable plenum of the Tuxill patent can result in patient discomfort and skin irritation beneath the plenum.

OBJECTS AND SUMMARY OF THE INVENTION

It is an object of the present invention to provide improved alignment between a tracheostomy mask and a tracheostomy tube inserted in the neck of a patient.

It is another object of the present invention to provide improved alignment between a tracheostomy mask and a tracheostomy tube inserted in the neck of a patient without rigidly affixing the mask to the tracheostomy tube.

It is yet another object of the present invention to provide alignment between a tracheostomy mask and a tracheostomy tube inserted in the neck of a patient without creating an extended interface with the skin of a patient around the tracheostomy tube.

It is a further object of the present invention to provide a tracheostomy mask which ensures reliable delivery of gaseous therapeutics to a patient fitted with an tracheostomy tube.

In accordance with one form of the present invention, a tracheostomy mask is formed having a stabilizer which is affixed to the mask body. The stabilizer is selected and positioned to receive a tracheostomy tube and maintain alignment between the tracheostomy tube and the mask. The stabilizer may be affixed to the mask by various means such as a plurality of small straps or by a substantially rigid member extending from a forward portion of the mask.

Previously, tracheostomy masks typically have been formed without means for aligning the mask to the tracheostomy tube. In these masks, the delivery of the medicament or humidification could be compromised if the alignment of the mask with the tracheostomy tube was disturbed. Those masks in the prior art which do provide some form of alignment structure suffer from significant disadvantages regarding patient comfort. The present invention provides a tracheostomy mask with alignment means which are not affixed to the tracheostomy tube and does not offer an extended, non-breathable interface to the skin of a patient. Therefore, a tracheostomy mask formed in accordance with the present invention features significantly improved reliability in medicament delivery without sacrificing patient comfort.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 2 is a perspective view of a tracheostomy mask with an alignment stabilizer, formed in accordance with the present invention.

DETAILED DESCRIPTION OF THE PREFERRED EMBODIMENTS

Figure 1A:
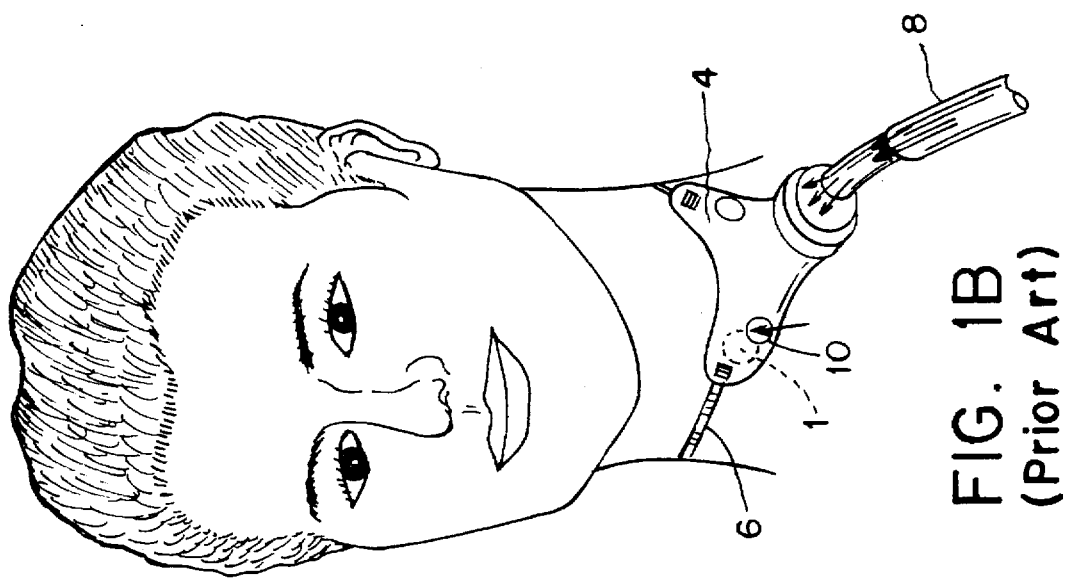
FIG. 1A is a perspective illustration of a tracheostomy mask, known in the prior art, shown in alignment with a tracheostomy tube in the neck of a patient.
Figure 1B:
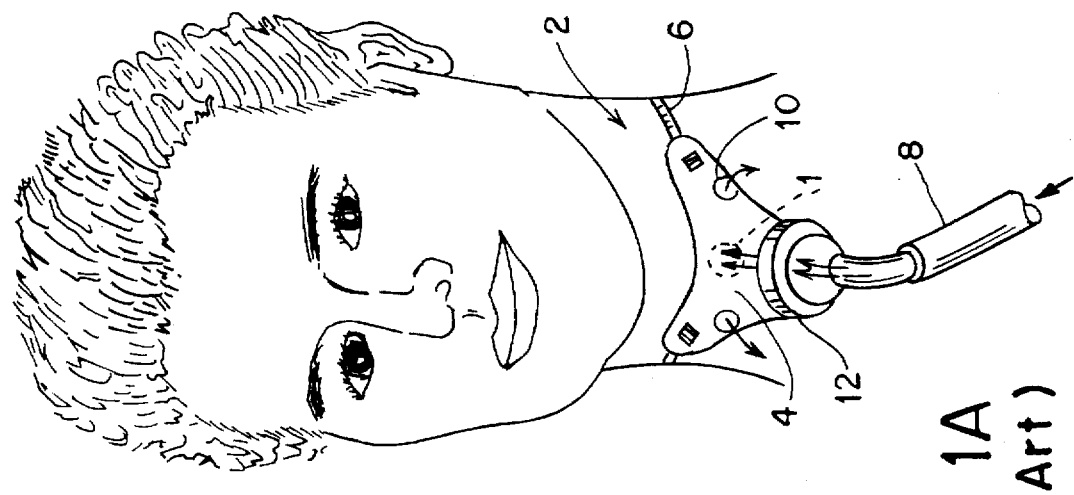
FIG. 1B is a perspective illustration of a tracheostomy mask, known in the prior art, shown out of alignment with a tracheostomy tube inserted in the neck of a patient.
Figure 3:
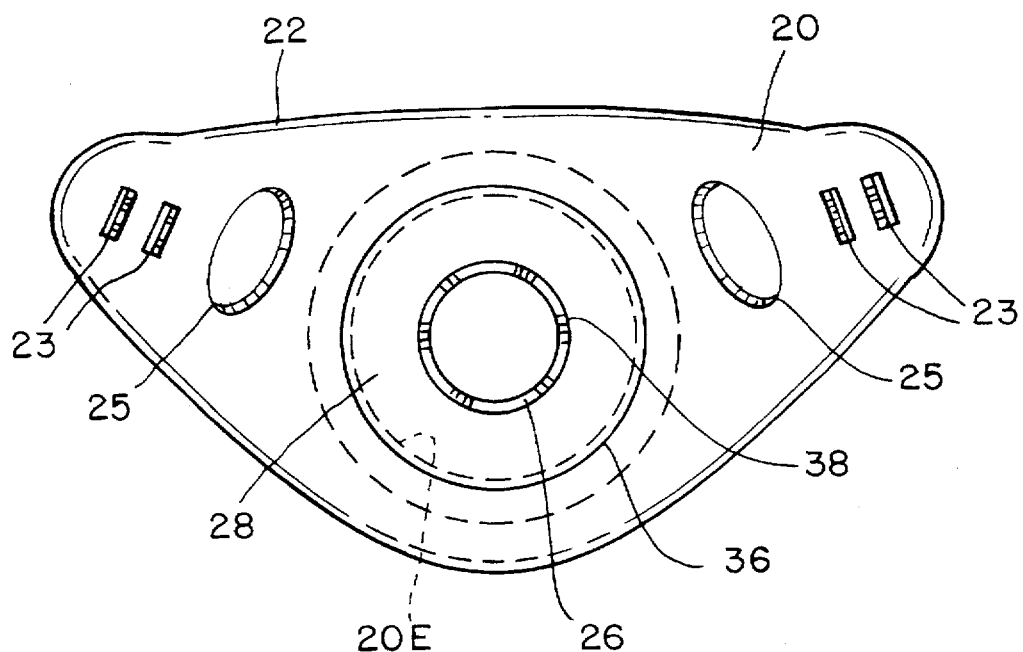
FIG. 3 is a top plan view of a tracheostomy mask with an alignment stabilizer, formed in accordance with the present invention.
Figure 4:
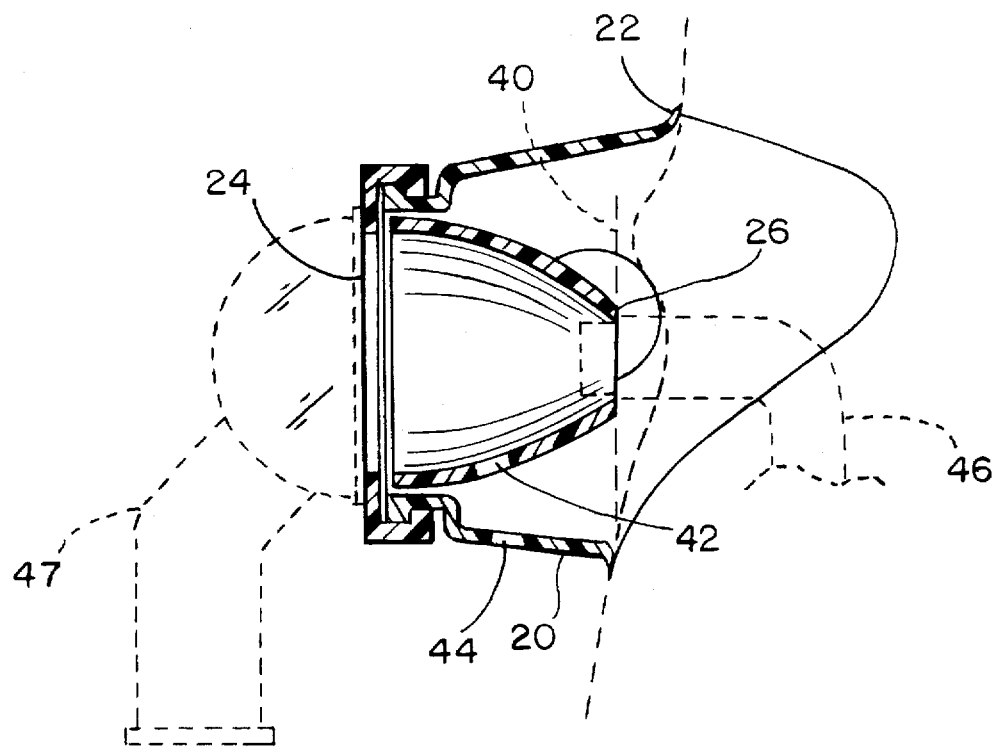
FIG. 4 is a cross-sectional view of a tracheostomy mask with an alignment stabilizer, formed in accordance with the present invention, and shown in cooperation with a tracheostomy tube inserted in the neck of a patient.

FIGS. 2, 3 and 4 illustrate a preferred embodiment of a tracheostomy mask with an alignment stabilizer formed in accordance with the present invention. The tracheostomy mask includes a flexible mask body 20. The mask body 20 is formed in the shape of a substantially continuous, cup-shaped wall. The mask body 20 has an interior surface 20A and an exterior surface 20B. When applied to a patient, the interior surface 20A is in communication with the patient and the exterior surface 20B is in communication with the ambient atmosphere.

Preferably, the mask is held against the neck of a patient by a thin elastic strap 21. The strap 21 is affixed to the mask body 20 by conventional means, such as threading the strap 21 through parallel slots 23. Alternatively, snaps, "VEL-CRO" (™) hook and loop fasteners, clips or other conventional fasteners may be used for affixing the strap 21 to the mask body 20.

The mask body 20 includes a rear portion 20C which terminates in an opening defined by a perimeter 22. The perimeter 22 is sized and shaped for sealable engagement against the neck of a patient. The cup-shaped wall of the mask body 20 extends away from the rear portion 20C and terminates in a forward portion 20D. Preferably, the mask body tapers throughout this extension.

The mask body 20 may further include one or more vent holes 25. The vent holes 25, which are illustrated in FIG. 3, aide in the prevention of condensation build up within the mask body 20.

The forward portion of the mask body 20 is perforated with an opening 20E for the infusion of therapeutics to a patient. A coupling ring 24 is affixed to the exterior surface 20B or the interior surface 20A of the mask body 20 and is disposed about the opening 20E in the forward portion 20D of the mask body 20. The coupling ring 24 is designed to receive a preferably rotatable adaptor suitable for interfacing with a conventional therapeutic supply tube.

In accordance with the present invention, a tracheostomy mask of FIGS. 2, 3 and 4 further includes an alignment stabilizer 26 and a support member 28. The stabilizer 26 includes an opening to receive the end of a tracheostomy tube. Preferably, the opening in the stabilizer 26 is substantially circular and has a diameter which is selected to be slightly larger than that of the tracheostomy tube. This allows the stabilizer 26 to receive the tracheostomy tube and provide the required alignment without rigidly affixing the mask body 20 to the tracheostomy tube.

The support member 28 is interposed between the stabilizer 26 and the mask body 20. The support member 28 is affixed to the mask body 20 to provide alignment and mechanical stability to the stabilizer 26. The support member 28 is affixed to the stabilizer 26 to maintain the stabilizer 26 in a position substantially centered within the perimeter 22 of the mask body rear portion.

In the embodiment illustrated in FIGS. 2, 3 and 4, the stabilizer 26 and support member 28 are formed as a unitary tubular structure 30. The tubular structure 30 is formed from a thin continuous wall which has an inner surface 32 and an outer surface 34. The tubular structure 30 further includes a first end 36 defined by a first perimeter and a second end 38 defined by a second perimeter. The first end 36 and second end 38 are in fluid communication with each other through a chamber defined by the inner surface 32 of the tubular structure 30.

The first end 36 of the tubular structure 30 is affixed to the mask body 20. The first end 36 is affixed such that the first perimeter surrounds the opening 20E in the forward portion 20D of the mask body 20. The second perimeter is sized and shaped to receive a tracheostomy tube. In this embodiment, the second end 38 of the tubular structure 30 functions as the stabilizer 26. Because the tracheostomy tube typically has a smaller diameter than that of the opening 20E in the mask body, the tubular structure 30 preferably is formed as a frustoconical structure wherein the second perimeter of the tubular structure 30 is smaller than the first perimeter.

Referring to FIG. 4, the second perimeter of the fracteconical structure 30 defines a plane 40. The second end 38 of the frustoconical structure 30 is shaped such that when the mask body 20 is properly engaged about the neck of a patient, the plane 40 is substantially parallel with the neck of the patient. It will be understood that depending on the contouring of the mask body 20, which is not critical to the present invention, the shape of the second end 38 may vary to obtain the desired parallel alignment with the neck of the patient.

FIG. 4 illustrates a tracheostomy mask of the present invention shown in cooperation with a tracheostomy tube 46 inserted within the neck and airway of the patient 22. As this cross sectional view illustrates, a forward extension of tracheostomy tube 46 is received by the stabilizer 26. Because the diameter of the opening of stabilizer 26 is selected to be larger than the outside diameter of the tracheostomy tube 46, the mask body 20 is free to move slightly without applying uncomfortable forces to the tracheostomy tube 46. In the event that significant force is inadvertently applied to a supply tube 47 attached to the coupling ring 24, the mask is allowed to pull away from the tracheostomy tube 46 without moving or dislodging the tracheostomy tube 46.

Preferably, the tracheostomy mask of FIGS. 2, 3 and 4 further includes a first weep hole 42 and a second weep hole 44. The weep holes 42, 44 provide drainage for fluids which may accumulate within the mask. The first weep hole 42 is created by perforating the wall of the fracteconical structure 30. The second weep hole 44 is formed by perforating the wall of the mask body 20. The first weep hole 42 and second weep hole 44 are positioned to be in substantial alignment to facilitate drainage of both the mask body 20 and support member 28. The first and second weep holes are preferably positioned such that when the tracheostomy mask is engaged about the neck of the patient, the weep holes are at the bottom most portion of the mask (i.e., directed towards the patient's feet). This allows mucous, phlegm and excess condensation to drain naturally by gravity, thereby preventing occlusion of the airway provided by the tracheostomy tube 46.

Figure 6:
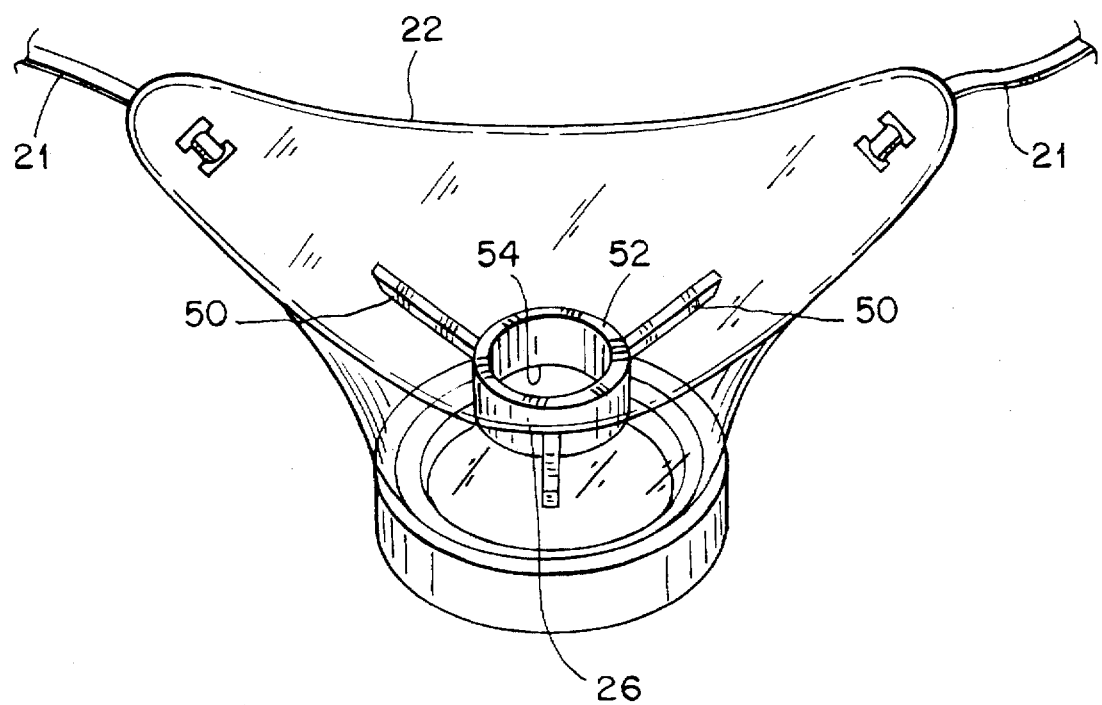
FIG. 6 is a perspective view of an alternate embodiment of a tracheostomy mask with an alignment stabilizer, formed in accordance with the present invention.
Figure 5:
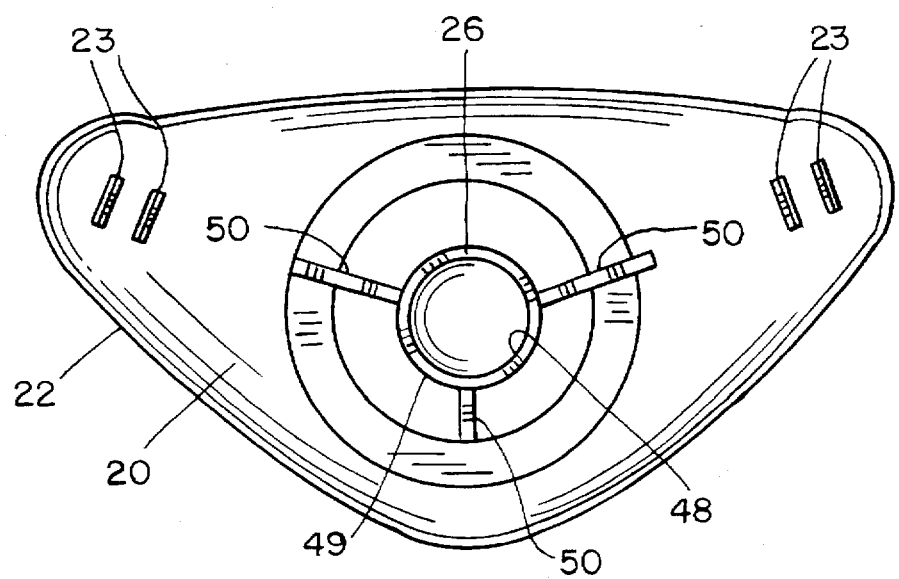
FIG. 5 is a top plan view of an alternate embodiment of a tracheostomy mask with an alignment stabilizer, formed in accordance with the present invention.

Alternate embodiments of the stabilizer support member are illustrated in FIGS. 5 and 6. The stabilizer 26 shown in FIG. 5 is formed as a substantially circular, planar ring. The ring has an inside perimeter 48 which is sized and shaped to receive an tracheostomy tube. The ring also includes an outside perimeter 49. The width of the stabilizer 26, which is defined by the difference between the inside and outside perimeter, is selected to provide sufficient mechanical stability to the stabilizer 26.

The stabilizer support member 28 (FIGS. 2–5) is formed from at least one elongate support 50. The elongate supports 50 have a first end which is attached to the outside perimeter 49 of the stabilizer 26 and a second end which is attached to the mask body 20. The width of the individual elongate supports 50 is not critical. If the elongate supports 50 are affixed proximate the perimeter 22 of the mask body 20 (such that the elongate supports will contact the patient's neck), the width should be selected to minimize the surface area of interface with the patient's neck. While three elongate supports 50 are illustrated, the number of elongate supports 50 used is not critical.

FIG. 6 illustrates an alternate embodiment wherein the elongate supports 50 are attached to a position on the interior surface 20A of the mask body 20. This configuration insures only minimal contact between the stabilizer 26, elongate members 50 and the skin of the patient. The width of the elongate members 50 in this embodiment are selected to provide the required stability to the stabilizer 26. The elongate supports 50 may be substantially rigid, or may take the form of flexible straps.

To allow the elongate supports 50 to be set back from the perimeter 22, the stabilizer 26 is formed as a substantially cylindrical tubular member. The tubular member has a forward portion 52 which is sized and shaped to receive a tracheostomy tube. The tubular member also includes a rear portion 54. The elongate members 50 are affixed proximate the rear portion 54 and maintain a position of the stabilizer 26 such that the forward portion 52 engages a tracheostomy tube when the mask is affixed to a patient. While three elongate members 50 are illustrated, the number of elongate members 50 used is not critical. Preferably, the elongate members 50 and stabilizer 26 are molded as a unitary structure with the mask body 20.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A tracheostomy mask for delivering gaseous therapeutics to a patient fitted with an tracheostomy tube, the mask comprising:

a mask body, the mask body having a forward portion, a rear portion, and an interior surface extending between the rear and forward portions, the interior surface being in communication with a tracheostomy tube when the mask is engaged on the neck of the patient, the rear portion having a perimeter for sealing engagement with the neck of a patient, the forward portion having an opening for receiving gaseous therapeutics;

a stabilizer, the stabilizer receiving a tracheostomy tube affixed to a patient; and stabilizer support means, the stabilizer support means affixing the stabilizer to the mask body in a position to receive and align the tracheostomy tube, the stabilizer support means being sized, shaped and positioned to minimize contact between the patient and the stabilizer support means.

2. A tracheostomy mask, as defined by claim 1, wherein:

the stabilizer further includes a stabilizer body, the stabilizer body having an outer perimeter and an opening, the opening selected to be larger than an outer diameter of a tracheostomy tube; and the stabilizer support means further comprises at least one elongate member, each elongate member having a first end and a second end, the first end being affixed to the outer perimeter of the stabilizer body and the second end being affixed to the mask body.

3. A tracheostomy mask for delivering gaseous therapeutics to a patient fitted with a tracheostomy tube, the mask comprising:

a mask body, the mask body having a forward portion, a rear portion, and an interior surface extending between the rear and forward portions, the interior surface being in communication with a tracheostomy tube when the mask is engaged on the neck of the patient, the rear portion having a perimeter for sealing engagement with the neck of a patient, the forward portion having an opening for receiving gaseous therapeutics; and a stabilizer, the stabilizer comprising a tubular member having a first end, a second end and a length, the first end having a first opening diameter and the second end having second opening diameter, the second opening diameter being selected to receive the tracheostomy tube, the first end being affixed to the interior surface of the mask body proximate the forward portion and positioned such that the first opening diameter encompasses the forward portion opening of the mask body, the length being selected such that when the mask is properly engaged on the neck of a patient the second end engages the tracheostomy tube.

4. A tracheostomy mask, as defined by claim 3, wherein the tubular member is formed as a frustoconical member with the first opening diameter being larger than the second opening diameter.

* * * * *